(12) United States Patent
Tyler

(10) Patent No.: US 6,306,103 B1
(45) Date of Patent: Oct. 23, 2001

(54) BLOOD/BODY FLUID COLLECTION APPARATUS AND METHOD

(76) Inventor: Sheila L. Tyler, 8369 Morningdew Dr., Reynoldsburg, OH (US) 43068

( * ) Notice: Subject to any disclaimer, the term of this patent is extended or adjusted under 35 U.S.C. 154(b) by 0 days.

(21) Appl. No.: 09/476,886

(22) Filed: Jan. 3, 2000

(51) Int. Cl.[7] .................................................. A61B 5/00
(52) U.S. Cl. ................................................... 600/573
(58) Field of Search ..................................... 600/573, 576, 600/578, 579; 604/187, 196, 197, 198

(56) References Cited

U.S. PATENT DOCUMENTS

| 5,135,489 | * | 8/1992 | Jepson et al. | 604/48 |
| 5,536,262 | * | 7/1996 | Valasquez | 604/283 |
| 5,611,782 | * | 3/1997 | Haedt | 604/198 |

* cited by examiner

*Primary Examiner*—Eric F. Winakur
*Assistant Examiner*—Pamela Wingood
(74) *Attorney, Agent, or Firm*—Robert E. Stebens

(57) ABSTRACT

Apparatus and a method of its use is disclosed for transfer of blood/body fluid from a fluids obtaining device which is placed in communication with a patient's body cavity containing the fluid desired to be obtained for analysis and depositing it in a collection container for storage and/or transport. The fluids obtaining device has a fluids retention component adapted to be alternatively coupled with either a sharp ended needle for penetrating a patient's body or a blunt ended cannula. A fluids displacing mechanism is positioned in the retention component and is reciprocated to either draw fluid from the patient into the retention component or to expel fluid therefrom. After drawing fluid from the patient, the needle is removed and replaced with the cannula. A closure member secured to an open end of the container includes a plug formed from an elastomeric material exhibiting the characteristics of being penetrable by the cannula and self resealable after withdrawal of the cannula. Removal of the needle is effected by a needle gripping mechanism associated with a "sharps" receptacle to avoid finger contact with the needle. The cannula is inserted through the plug into the container and the fluid expelled from the retention component. The cannula is then withdrawn from the plug with minimal likelihood of an accidental "stick" and discarded along with the fluids obtaining device.

11 Claims, 4 Drawing Sheets

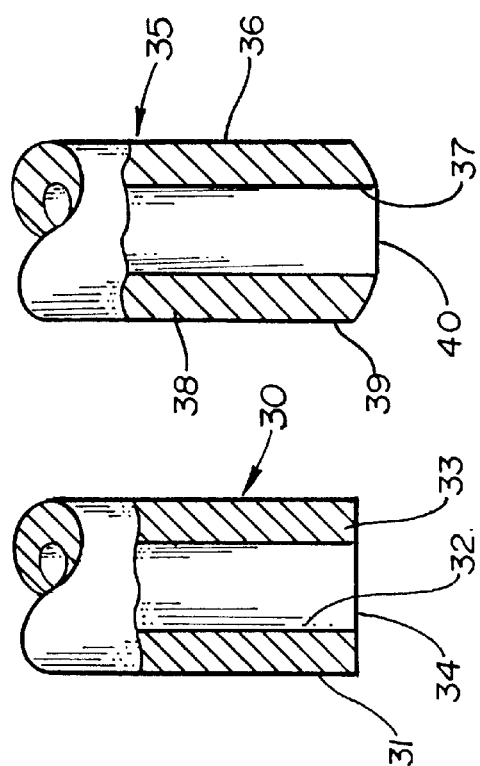
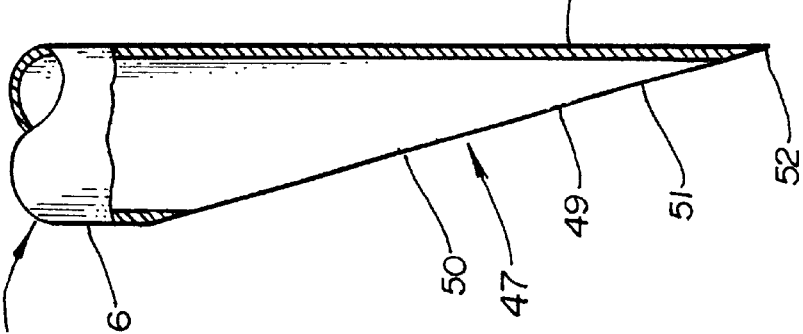
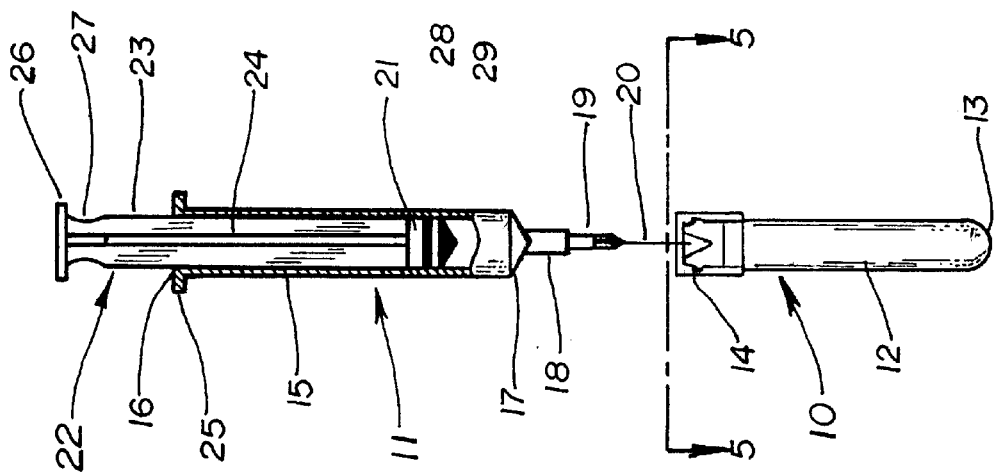

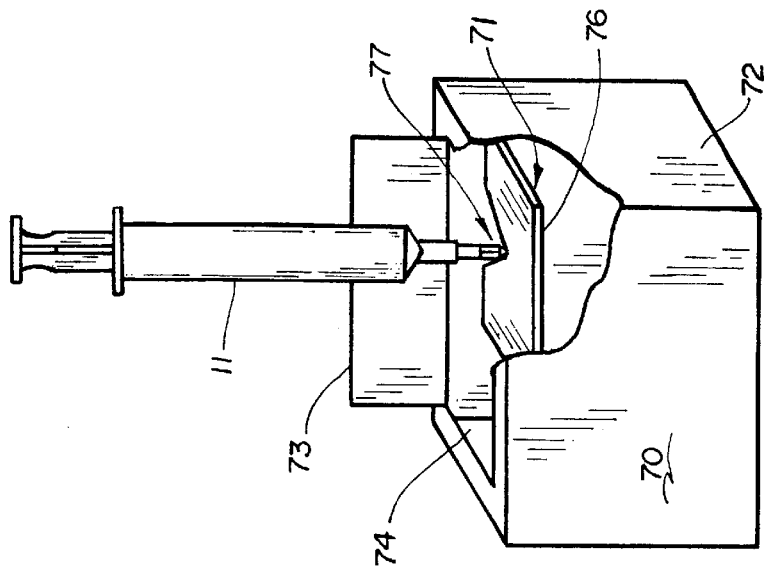
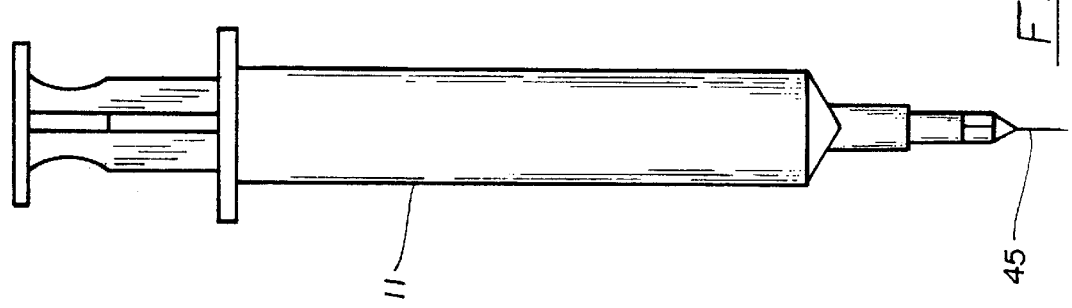
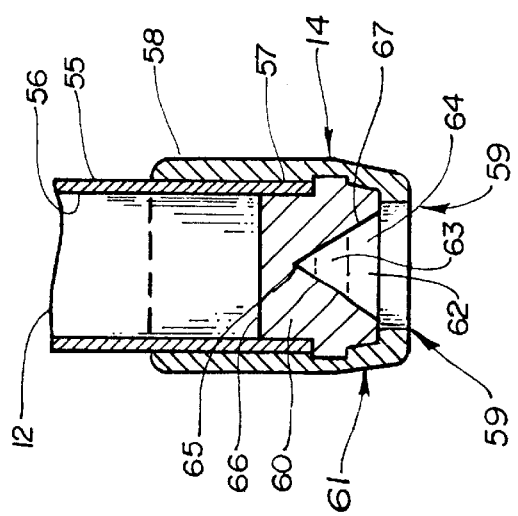
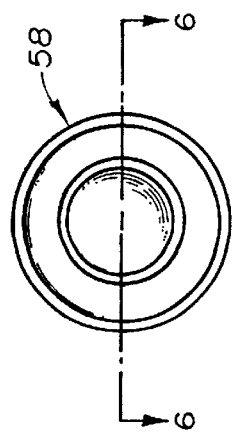

BLOOD/BODY FLUID COLLECTION APPARATUS AND METHOD

FIELD OF THE INVENTION

This invention relates generally to blood/body fluid collection apparatus and to a method of utilizing that apparatus in drawing blood/body fluids from the body for minimizing accidental injection of the drawn blood/body fluid into the health care worker performing a blood/body fluid procedure. It relates in particular to blood/body fluid drawing apparatus and method of its use which eliminates utilization of the sharp pointed needle when effecting transfer of the blood/body fluid from the drawing syringe to the blood/body fluid specimen collection container. The invention apparatus and method substitutes a blunt ended cannula for the sharp needle when performing the transfer operation through providing of a collection tube closure that is penetratable by a blunt ended cannula and which is self-resealable upon its withdrawal.

BACKGROUND OF THE INVENTION

A common procedure in the medical field is drawing of blood/body fluid specimens from a patient for laboratory analysis to assist in diagnosing of the patient's medical symptoms. The use of a syringe and needle is commonly used by direct venepuncture, or with use of a central or established peripheral intraveneous line (IV). Direct venepuncture uses a syringe fitted with a sharp pointed needle for penetrating the body and insertion into a vein, artery, spinal column, or body cavity. Peripheral/Central intravenous lines are also accessed with a syringe and a sharp pointed needle. The syringe is screwed onto the hub of the intravenous line and blood is withdrawn. A sharp pointed needle is then attached. Operating the syringe in an extracting mode effects withdrawal of a quantity of blood/body fluids from the patient and it is temporarily stored in the syringe's tubular body. After drawing the desired quantity of blood, the health care worker then extracts the syringe and needle from the patient or unscrews the syringe from the hub of the central or peripheral intravenous line and attaches a needle in preparatory to transfer of the just drawn specimen to a blood/body fluid collection container. Blood/body fluid collection containers are of tubular configuration provided at their open end with a closure that is gas impermeable although, in accordance with prior art, it is puncturable by the sharp-pointed end of a needle.

It is desirable that the closure member be gas impermeable, as is the collection container, since the collected blood/body fluid specimen is preferably stored in a closed container from which ambient air has been evacuated. Thus, a collection container, prior to receiving a blood/body fluid specimen, is essentially an empty void representing a vacuum. Ambient air contains or carries oxygen, carbon dioxide, nitrogen and other gaseous materials in addition to particles of various solid substances, all of which tend to contaminate the blood/body fluid specimen. Consequently, a blood/body fluid specimen may be contaminated with foreign substances which could adversely affect test results thereby resulting in erroneous diagnosis of a patient's symptoms through analysis of the collected blood specimen unless an evacuated collection container is utilized for receipt and storage of the specimen.

Having collected a blood/body fluid specimen in the syringe's body, the health care worker, then transfers that specimen into the blood/body fluid collection container. It is this step of the procedure which subjects the health care worker to the greatest hazard or risk. Recognizing the needle has now at least been in contact with, if not actually carrying a patient's blood/body fluid which must be considered as having infectious disease virus, the health care worker must now exercise extreme caution in all subsequent operations. Two of the most dangerous viruses that may be present in the blood/body fluid specimen are the HIV/AIDS and Hepatitis B or C strains. As previously noted, prior art closures members for collection containers are puncturable, and are only puncturable, by sharp-pointed needles.

The first step in effecting transfer of the specimen from the syringe to the collection container is insertion of the syringe's needle through the transverse end of the closure member in a generally axial direction relative to the collection container's tubular body. This presents a first instance where the technician may experience an accidental piercing of a finger by the needle, or perhaps another part of the hand that is holding the collection container, thereby becoming infected with a virus carried by the blood/body fluid specimen that has just been drawn. An accidental stick could also occur as a consequence of the health care worker making an error in physically manipulating the components while picking up a collection container and bringing it and the needle into proximate relationship to the collection container preparatory to inserting the needle into the container through the closure member.

A second instance when an accidental needle stick may occur is after ejecting the blood/body fluid sample from the syringe into the collection container and then withdrawing the needle from the closure member. The closure members for these collection containers is usually fabricated from an elastomeric material of a type that is self-resealable whereby it closes the opening previously made by the needle thereby maintaining the vacuum state in the collection container space that has not been filled with the just drawn blood/body fluid specimen. These closure members are usually formed from an elastomeric material tending to maintain a tight, compressive engagement with the exterior surface of the needle as is desired to assure the vacuum will be effectively maintained in the collection container. This also effectively prevents entrance into the container of ambient air containing gaseous materials and solid particles that would likely contaminate the blood/body fluid specimen. When the health care worker begins pulling the needle axially out of the closure member, considerable force must be applied to overcome the frictional force existing between the needle and the closure member. It is when the needle is nearly fully withdrawn from the closure member that a critical stage in the withdrawal operation is reached where one is likely to encounter an accidental needle stick to the finger or hand thereof. This results from the fact that as the tapered end of the needle exits through the closure member the frictional force rapidly diminishes since the surface area of the needle decreases due its tapered configuration; but, the health care worker tends to experience momentary loss of directional or speed control, or both, of the needle. This loss of control may often be of such extent as to cause an accidental sticking by the contaminated syringe's needle into a health care worker's finger on the hand holding the collection container.

A number of circumstances enter into effecting this loss of control with one major factor being that the health care worker has no accurate means of determining when the terminal end portion of the needle will exit the closure member. The terminal end portion of the needle is still within the collection container where it is concealed from view by the closure member which is invariably fabricated from an opaque material. As a result, the health care worker cannot precisely determine when the needle is in position to begin exiting the closure member and is not likely to be fully prepared to timely react appropriately to the unpredictable movement of the needle as it exits from the closure member. Another factor is the diminishing surface area of the needle in frictional engagement with the closure member as the terminal end of the needle passes through the membrane of the closure member. This results from the fact that the terminal end of the needle tapers to a sharp point thereby reducing the axially directed force necessary to effect its withdrawal. However, a health care worker is not aware of when a lesser force is required and does not reduce the extracting force resulting in an increase in the extracting speed of the needle, thus compounding the problem. Also, the health care worker is usually holding the syringe in a manner which provides minimal directional control over a needle that may be moving in an erratic fashion.

All blood/body fluid specimens drawn from patients are deemed to include infectious disease virus. Accordingly, the health care worker involved with drawing of blood/body fluids specimens, or their subsequent handling and processing, observe certain safety protocols which have been established to enhance minimization of transmission of these devastating diseases. This problem of becoming accidently infected is of no small significance when one considers the number of accidental needle sticks that occur annually along with the seriousness of the consequences that can result. A first and primary concern is the health of the health care worker who has incurred a needle stick. Soon after receiving a stick the health care worker must initiate precautionary procedures and ongoing monitoring to counteract the possibility of having become infected with a devastating, if not deadly, virus.

An example of a prior art biological liquid container having what is designated as a safety closing device is disclosed in U.S. Pat. No. 5,433,716 granted Jul. 18, 1995 to Leopard, et al. That device includes two cooperating components of circular disc form disposed in superposed relationship over the open end of a container to which they are removably secured. One of discs identified by the numeral 4 remains on the container at the time of effecting transfer of a liquid into the container and is made of a perforable material but it is fabricated with a transversely extending incision identified by the numeral 8 that extends through the disc. This incision is formed in a manner whereby its opposing surfaces extend into contacting engagement thus forming a hermetic seal. The specification of this patent only describes use of sharpened "needle" for insertion through the incision in effecting a blood/body fluid drawing procedure.

Other known prior art disclosures and apparatus, whether patented or not, are all of a type which utilize a sharpened needle. Some of the patent disclosures refer to the device that is inserted through a container's closure member as being a "cannula". But, the drawings of those patents only show use of a sharp needle in effecting transfer of blood/body fluid to a collection container and their respective descriptions do not provide either a direct indication or even a remote suggestion that the cannula should or could be other than a sharp needle.

SUMMARY OF THE INVENTION

This invention is directed to both the structure of the blood/body fluid collection container, particularly its closure member, and to the method of manipulating the blood/body fluid drawing syringe. The collection container includes a structurally rigid, elongated tubular main body that is closed at one end and open at its opposite end and to a closure member that is designed to interfit with the container at its open end in mechanically secured engagement. Both the tubular container and the closure member are fabricated from gas impermeable materials to enable maintenance of a vacumn within the interior of the collection container. In accordance with the illustrative embodiment of this invention the closure member is formed with a plug that interfits in fluid tight engagement in the container's open end with this plug being formed from an elastomeric material that is penetrable by sharp-pointed syringe needles as well as blunt end cannulas. This plug is formed from an elastomeric material which also exhibits the characteristic of being self-resealable at the point where it was previously penetrated by either a needle or a cannula when that device is withdrawn from the plug. It is this characteristic that effects maintenance of a vacumn in a collection container when performing a blood/body fluid collection procedure.

Drawing of a blood/body fluid specimen utilizing the method of this invention is a two step procedure which utilize a syringe with a sharp needle during the step which is drawing of the specimen from the patient. Whether using direct venepuncture or an established intravenous line a syringe and needle are utilized. Next, the specimen is transferred from the syringe to the collection container. With direct venepuncture, after obtaining the specimen, the sharp pointed needle is removed and disposed of in a "sharps" container for subsequent safe disposal. A blunt ended cannula is then attached to the syringe for effecting transfer of the specimen. A sharp pointed needle would not have to be used with accessing an established intravenous line. A syringe is screwed onto the hub of the IV line and blood/body fluid is withdrawn. A blunt ended cannula is then attached to the syringe in preparation to transfer of the specimen. While holding a blood/body fluid collection container in one hand, the health care worker can then move the syringe to a position for inserting the blunt ended cannula through the closure member's central membrane without particular concern for incurring an accidental "stick" in the finger or other part of the hand that is holding the container. More importantly, the method of this invention in combination with the novel structure of the collection container is uniquely capable of essentially eliminating the likelihood of a "needle" stick occurring during the operational stage of transferring the blood/body fluid specimen from the syringe into the collection container.

After the cannula has been inserted through the closure members central membrane and the specimen expelled into the container, the health care worker then proceeds to withdraw the cannula from the closure member. Again, while the health care worker cannot predict the exact moment when the cannula will exit from the closure member this is not a matter of particular concern. Even though the health care worker may momentarily lose precise directional control over the path of movement of the cannula as a consequence of its outer terminal end rapidly springing free from the closure member, it is not a matter of real concern. If the cannula's terminal end should be displaced a sufficient distance transversely across the end of the closure member to become positioned laterally outward from the closure member, it is not likely that axial displacement of the cannula bringing its terminal end into contacting engagement with the health care worker's hand holding the collection container, or a finger of that hand, will result in an injury. The cannula having a blunt terminal end would only be able to puncture the glove and flesh of the health care worker if an extreme amount of force were applied to the cannula. This is not likely to happen since the health care worker has been applying an oppositely directed axial force and it would be highly improbable the health care worker would change direction of force application at this stage of the operation. Furthermore, if the terminal end of the cannula should be brought into contacting engagement with either the health care worker's hand or a finger, the blunt end of the cannula is only likely to exert a warning pressure force to the health care worker.

Combination of the apparatus and the method of performing a blood/body fluid drawing operation in accordance with this invention is highly effective in eliminating accidental "sticks". Consequently, this invention achieves the significant advantage over prior art blood/body fluid drawing apparatus of reducing hazard to a health care worker and, thereby, enhancing occupational safety in the field of medicine. Also, the technique of this invention retains a high degree of simplicity in its operation and does not result in a significant increase in cost of materials or a health care workers time in performance of the procedure.

These and other objects and advantages of this invention will become more fully apparent from the following detailed description of embodiments of the apparatus and the method of this invention along with the accompanying drawings.

DESCRIPTION OF THE DRAWING FIGURES

FIG. 1 is an elevational view of a blood collection container and a syringe provided with a blunt end cannula embodying this invention and disposed in axial alignment as either preparatory to interengement or as subsequent to disengagement of the cannula from the closure member.

FIG. 2 is a fragmentary side view on an enlarged scale of the distal end portion of the blunt end cannula shown in FIG. 1 with portions thereof broken away for clarity of illustration of its structure.

FIG. 3 is a fragmentary side view on an enlarged scale of the distal end portion of a modified blunt end cannula with portions thereof broken away for clarity of illustration of its structure.

FIG. 4 is a fragmentary side view on an enlarged scale of the distal end portion of a sharp end cannula of a configuration designed for intravenous penetration with portions thereof broken away for clarity of illustration of its structure.

FIG. 5 is a top end view on an enlarged scale of the container taken along line 5—5 of FIG. 1.

FIG. 6 is a medial sectional view taken along line 6—6 of FIG. 5.

FIG. 7 is a diagrammatic illustration of a syringe body fitted with a needle for a blood/body fluid drawing procedure.

FIG. 8 is a diagrammatic illustration of removal of a contaminated needle from a syringe's tubular main body and discard thereof into a sharp's container.

DESCRIPTION OF THE ILLUSTRATIVE EMBODIMENTS AND METHOD

Figure 11:
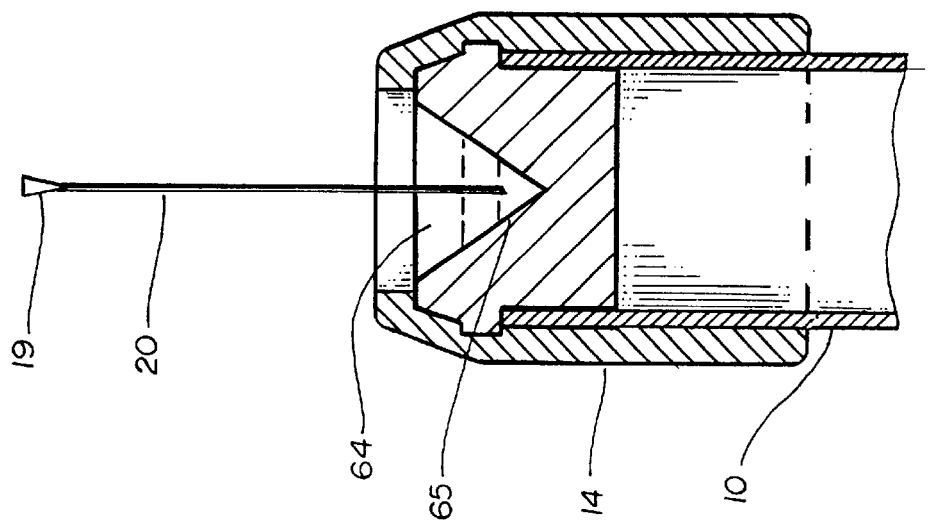
FIG. 11 is a diagrammatic illustration of a syringe with its cannula positioned in a plug's socket with the cannula's distal end at the socket's apex.

Referring to FIG. 1, a blood collection container 10 and a syringe 11 embodying this invention are shown positioned in vertically upright, axially aligned relationship to each other as they would be located during the course of a blood transferring operation. The container comprises an elongated tubular body 12 that is closed at its one end by an integrally formed, arcuately configured end wall 13. It is preferably fabricated from a suitable plastic material, such as transparent acrylic plastic that exhibits adequate structural strength and resistance to breakage. Secured to the upper end of the container, which is open, is a closure member 14 that is described in greater detail with reference to FIGS. 5 and 6.

The syringe 11 is of conventional construction for this type of medical device and includes an elongated, tubular main body 15 open at its upper end 16 and provided with an integrally formed lower end wall 17. This end wall is of a conical configuration and oriented to extend in an axially outward direction from the main body 15 with which it is coaxially positioned. A connector fitting 18 is provided at the apex of the end wall and comprises a structure that is of a design to removably interconnect in mechanically secured engagement with a mating fitting 19 attached to the proximal end of a coaxially extending cannula 20.

The syringe 11 shown in FIG. 1 is illustrative of a typical syringe and is not to be considered limitative as to the type or particular construction of the syringe which may be preferred for use in any specific instance. This illustrated syringe has a piston 21 carried on one end of an elongated piston rod 22 with that combination being axially displaceable through the tubular body 15. Forming the piston rod are four integrally formed, axially extending plates 23 disposed in angularly spaced relationship to each other and extending radially outward from a central axis where they are interconnected. These plates extend a distance radially outward to place their outer edges 24 in contacting engagement with the interior wall surface of the tubular body thereby maintaining the piston rod in coaxial alignment during the course of its axial displacement in either a fluids drawing or expelling operation. Integrally formed with the tubular body at its upper end 16 is a coaxially disposed annular flange 25 which extends a short distance radially outward from the body thereby providing a surface that may be engaged at its lower surface by the operator's fingers when manipulating the syringe. A circular plate 26 is formed on the outer end of the piston rod against which the operator places their thumb when pushing the piston rod 22 and piston 21 inwardly to expel fluid from the syringe. There are arcuate indentations 27 formed in each of the piston rod's plates 23 closely adjacent the circular plate 26 to facilitate positioning of the worker's fingers under that circular plate when pulling the piston rod and its piston upwardly in effecting drawing of fluid into the syringe's tubular body 15. The piston 21 includes an elastomeric terminal end component 28 for forming a fluid-tight seal with the interior surface of the tubular body which is cylindrical. It is formed with a conically shaped axial end face 29 which mates with the end wall 17 of the body 15 thus ensuring that all of the fluid can be expelled from the syringe's tubular body. In this exemplary embodiment, the syringe's tubular body is fabricated from a transparent material, such as acrylic plastic, thereby enabling the worker to be appraised of the quantity of fluid which has been drawn or expelled. Appropriate volumetric indicia are typically imprinted on the tube's exterior for that purpose. A plastic of this type is generally used because it has adequate structural strength. It is also not costly thus enabling these syringes to meet the economic limitations of one time, throw away usage.

The term "cannula" broadly means a small diameter tube, particularly in the medical field, and commonly used for transfer of fluids. A cannula, in the context of this invention, is a tube having at least one end intended to penetrate a membrane or wall of a component of an apparatus or structure utilized in or with a medical procedure or process. It is not a tube having an end which is intended to penetrate the skin or flesh of a patient's body such as is the sharp end of a tubular needle utilized in penetrating a patient's vein for effecting either drawing of blood or injection of a fluid. In the context of the description of this invention, the term "cannula", unless specifically otherwise described, defines a small diameter tube having at least one end formed with a blunt configuration which is not likely to penetrate a patient's skin or flesh without application of a relatively great amount of axially directed force. The force required to effect penetration by a cannula is substantially greater than that necessary to effect penetration by a sharpened end needle. The opposite end of a cannula is formed or provided with structure designed to mechanically interfit with another component of the composite apparatus in fluid impervious relationship, either liquid or gaseous. In this description, a tube formed with a sharpened end is termed a "needle".

FIG. 2 illustrates on a greatly enlarged scale the physical structure of the distal end portion of a cannula 30 utilized in a structural embodiment of this invention and also in implementation of the inventive method. It is shown with portions broken away to more clearly illustrate the structure. The cannula comprises an elongated tube 30 formed from a suitable plastic or metal exhibiting adequate structural strength in addition to being resistant to corrosion and susceptible to sterilization. Length of a cannula is determined by dimensional criteria of the environment in which it is intended to be operated. Typical lengths are in the order of ¾" to 1½". Diameter of the outer surface 31 of cannulas for use in blood collection procedures are generally of the order of 1.0 mm with an internal surface 32 having a diameter of the order of 0.5 mm with the two surfaces thus defining a wall 33 having a thickness of 0.25 mm. The wall terminates in an annular end face 34 which engages the transverse end surface of a closure member 14 positioned on the open end of the tubular body 12 of a blood collection container 10 when effecting penetration thereof to transfer blood into or from the container.

A modified cannula 35 is shown in FIG. 3 that also may be utilized in implementing the method of this invention. This is a fragmentary portion of the cannula showing the distal end portion that penetrates a closure member 14. This cannula includes an elongated cylindrical tube having respective exterior and interior wall surfaces 36, 37 which cooperatively define a tubular wall 38. Dimensions of this cannula are also typically the same as those of the cannula 30 described in the preceding paragraph with reference to the cannula shown in FIG. 2. Cannula 35 is also fabricated from a material, such as stainless steel or plastic, capable of providing adequate structural strength, resist corrosion and susceptible to sterilization techniques. Although not shown, the opposite or proximal end of the cannula 35, as is the cannula 30, is fabricated with a mating fitting which cooperatively interfits with a syringe's connector fitting 18 in removable mechanical engagement therewith that is fluid impervious. The extreme terminal end 39 of this cannula has the marginal end portion of the wall turned inwardly thereby forming an arcuately configured, axial end face 40 which is designed to facilitate penetration of the closure member 14.

FIG. 4 illustrates a needle 45 of the typical configuration utilized for penetrating a patient's skin and flesh for insertion into a vein. It has an elongated, tubular main body 46 which terminates in a sharp, tapered distal end 47. The proximal end [not shown] is provided with a mating fitting designed to interfit in removable mechanical engagement with the connector fitting 18 mounted on the end wall 17 at the lower end of the syringe's tubular main body 15. This interconnection is also fluid impervious. The tubular main body 46 of the needle comprises a cylindrical wall 48 having an exterior surface 49 and an interior surface 50. The distal end 47 of the needle is formed by cutting the tubular body 46 transversely at an angle of the order of 30 degrees to the longitudinal axis of the needle resulting in formation of an obliquely disposed, annular end face 51 thereby forming a sharp point 52 at one side of the tubular body.

Referring to FIGS. 5 and 6, an embodiment of the closure member 14 is shown on a scale that is substantially enlarged in comparison to FIG. 1. It is shown positioned in operative relationship on the open end of a collection container's tubular body 12 which consists of a cylindrical tube having outer and inner wall surfaces 55, 56 terminating in an annular end face 57. The closure member comprises two components, a rigid tubular sleeve 58 and an elastomeric plug 59, that are of a design and configuration to mechanically interfit thereby forming a unitary structure. It is dimensioned so the sleeve partially fits over the container's body 12 in close fitting relationship with the remaining portion extending a distance axially outward from the tube's end face 57. The plug is cylindrical having a base section 60 and a coaxially aligned interlocking section 61 that are integrally formed. Its base section is of a diameter to contactingly engage the tube's inner wall surface 56 in frictional engagement to mechanically secure the plug in the tube and form a fluid impervious seal therewith. An annular flange 62 is formed around the plug's interlocking section immediately adjacent the base section and projects into a mating annular groove 63 formed in the sleeve 58. Through appropriate sizing of the diameters of the various portions of the exterior surfaces of the interlocking section 61 relative to the opposing interior surfaces of the sleeve 58, radially inward compression of the elastomeric material forming the plug 59 is obtained resulting in greater frictional engagement thereby increasing resistance to relative rotational movement therebetween. This effect is advantageous when assembling the closure member 14 with the container 10 or in separating them. Either of these operations is most easily accomplished by a combined rotational movement and axial displacement with respect to the container. This is of particular advantage if a subsequent analytical procedure to be performed on the specimen is best effected with removal of the closure member as there is less likelihood of spillage of the specimen when the plug 59 exits from the container.

Formed in the plug 59 is a conically shaped socket 64 with its base at the outer axial end surface 65 of the plug's interlocking section 61. The socket extends a distance coaxially inward of the plug with its apex 65 spaced a distance from the end wall 66 of the plug's base section 60. Sidewall 67 of socket 64 functions to guide a cannula toward the apex resulting in the cannula having a minimum thickness of the elastomeric plug to penetrate.

The closure member 14 described in the preceding paragraphs with reference to FIGS. 5 and 6 is considered exemplary of a device for that purpose. It is not to be considered limitative on the scope of the invention other than to the extent the plug 59 forms a fluid tight seal with the container 12 and is formed from an elastomeric material which exhibits the characteristics of being both gas impermeable and pentratable by a blunt end cannula as well as being self resealable after a penetrating cannula is withdrawn therefrom. Being gas impermeable is a necessary characteristic to maintain the container in a substantially air evacuated state thereby minimizing the likelihood of contamination of the specimen by contaminant gases.

With illustrative embodiments of components of the apparatus of this invention having been described with respect to designated drawing figures, operation of those components in performing a blood transferring operation employing the method of this invention is now described with reference to FIGS. 7 through 13. These drawing figures are diagrammatic as structure of the components is shown in substantial detail in FIGS. 1–6 and is also described in comprehensive detail with respect to those figures.

The first step is obtaining of a blood specimen from the patient and this requires that the syringe 12 be provided with a needle 45 as shown in FIG. 7 where that is the technique which will be employed in drawing the blood. While this introductory sentence uses the word "blood" it is to be understood that it is being used in a generic sense and encompasses other fluids in the course of employment of the method of this invention. Also, it is to be understood this inventive method is not limited in its scope of utilization to only drawing of blood from a patient. A fragmentary portion of a needle of this type is shown in FIG. 4 and designated by the numeral 45. When the body 12 of the syringe is not initially provided with a needle, the technician must first attach a needle to the connector fitting 18. At this stage of the procedure the technician is not faced with a significant health hazard since the needle, at this time, is sterile. An accidental stick with a sterile needle is certainly not to be casually dismissed but the technician is not faced with the consequences of a possible infection by a life threatening virus.

It is after the blood specimen has been drawn and the needle removed from the patient that the sharp point 52 and annular end face 51 along with the exterior surface 49 of the needle's main body wall 48 must be considered contaminated and appropriate precautionary procedures be thereafter followed. Procedure for transfer of the blood specimen from the syringe's tubular body 12 to the collection container 10 is now initiated. As the initial step, the technician removes the needle 45 from the syringe's body 12 and discards it into a "sharps" container 70 for ultimate disposal. A technique for removal of the needle utilizes a sharps container that is provided with a needle gripping mechanism 71. This technique is shown in FIG. 8 which illustrates a typical sharps container having a bottom receptacle 72 which retains the needle after its removal. A hinged lid 73 secured to the container at its top effects closing of its access opening 74 in addition to covering the needle gripping mechanism which must be considered contaminated as a consequence of having contacted a needle, presumed to be contaminated, during the course of a needle removing operation. A needle gripping mechanism 71 generally comprises a flat, structurally rigid plate 76 supported in a horizontal plane in the upper region of a sharps container at a position where it is accessible through the opening 74 in the receptacle's top. Formed in the plate 76 is a slot 77 of elongated, V-shaped configuration dimensioned to permit transverse passage therethrough of a needle 45 and its mating fitting 19 that is mechanically secured to a syringe's connector fitting 18. By sliding the mating fitting longitudinally of the slot 77 toward its apex, the fitting will become frictionally engaged with the side walls of the slot. When thus engaged, rotation of the syringe 11 results in decoupling of the connector fitting 18 from the mating fitting 19 thereby enabling the needle along with its fitting to be dislodged from the slot 77 and drop downwardly into the bottom receptacle 72. This frees the syringe's tubular body for the next step in the procedure.

Figure 10:
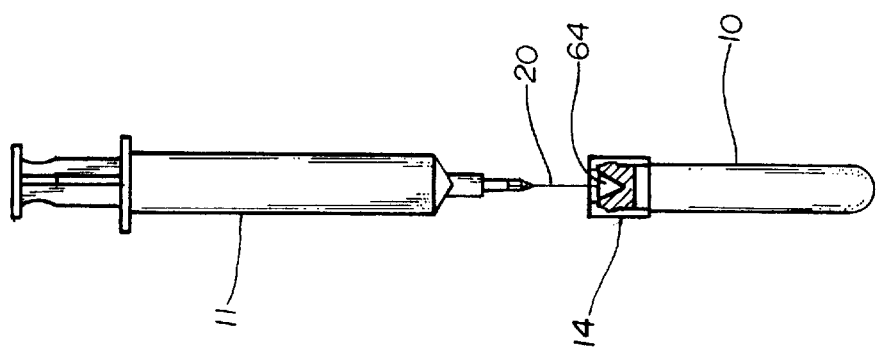
FIG. 10 is a diagrammatic illustration of initially positioning of a syringe having a cannula in axial alignment with a collection container and the plug's socket of its closure member.
Figure 9:
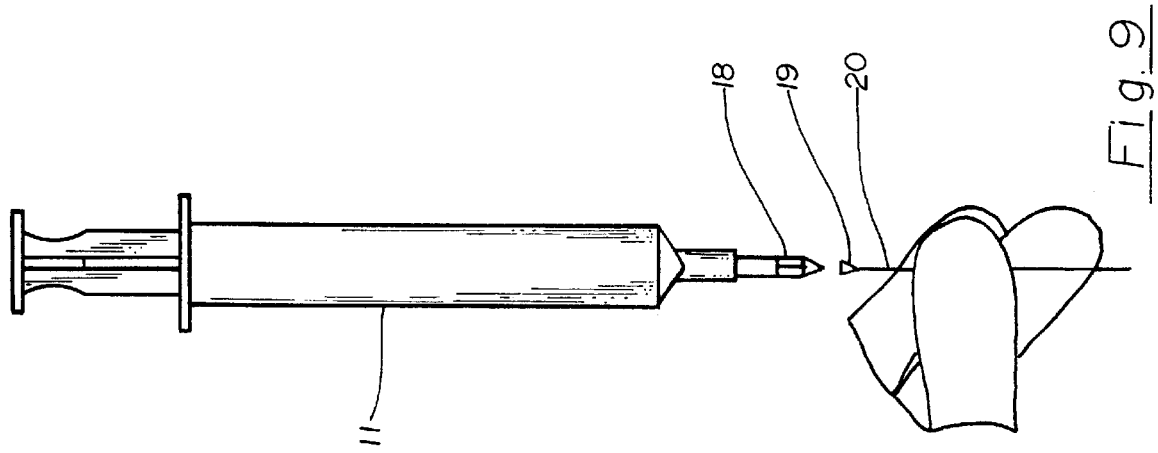
FIG. 9 is a diagrammatic illustration of attaching a cannula to a syringe's connector fitting.

At this point the health care person is ready to attach a blunt end cannula, such as either 30 or 35, to the syringe's tubular body 15 as is diagrammatically shown in FIG. 10. A cannula having an appropriate mating fitting 19 secured to its proximal end opposite its distal open end is removed from its package where it has been maintained in a sterile state. To assemble the cannula with the syringe's tubular body 15, the cannula is gripped by the fingers of the person's one hand to effect manipulation thereof in mechanically engaging its mating fitting 19 to the connector fitting 18. Recognizing that the person's hand, at this time, is protectively sheathed in a surgical glove, this manipulation is accomplished with relative safety. Any blood or other body fluid which may be contaminated is contained within the tubular body with the only portion exposed being that which is present in the connector fitting. While there is a possibility of the person performing the assembly operation contacting the blood or fluid in the connector fitting, this is not likely and, furthermore, presents a minimal hazard since the connector fitting is not formed with any sharp-pointed projection that would be expected to puncture either a surgical glove or a person's flesh. Also, the person performing the assembly operation is primarily exerting a rotative force on the cannula, not an axially directed force such as is required to effect puncturing.

With the cannula 30 affixed to the syringe's tubular body 15, the health care person is ready to proceed with the actual operation of transferring the blood or other body fluid specimen from the syringe to the collection container 10. With the syringe 11 held by the person in an operative position in one hand and a container 10 held in their other hand, the syringe and cannula are maneuvered to position the cannula in axial alignment with the container at its end provided with the closure member 14.

At this time, the health care person is at the stage in the fluids transfer operation to effect removal of the specimen from the syringe's tubular body 15 and displace it into the collection container 10. This stage of the operation is diagrammatically illustrated in FIG. 11. After first substantially coaxially aligning the syringe and its cannula 30 with the container 11 along their respective longitudinal axes, the syringe and container are axially displaced toward each other bringing the distal end of the cannula into contacting engagement with the conical surface 67 of the plug's socket 64 at its apex 65. The converging surface of the socket aides in guiding the distal end of the cannula to the socket's apex 65. It is not essential that the cannula be precisely coaxially positioned as a slight angular offset will not normally interfere with a penetration but it is advantageous as it minimizes the distance through which the cannula must be pushed in effecting penetration of the plug's base section 60.

Figure 12:
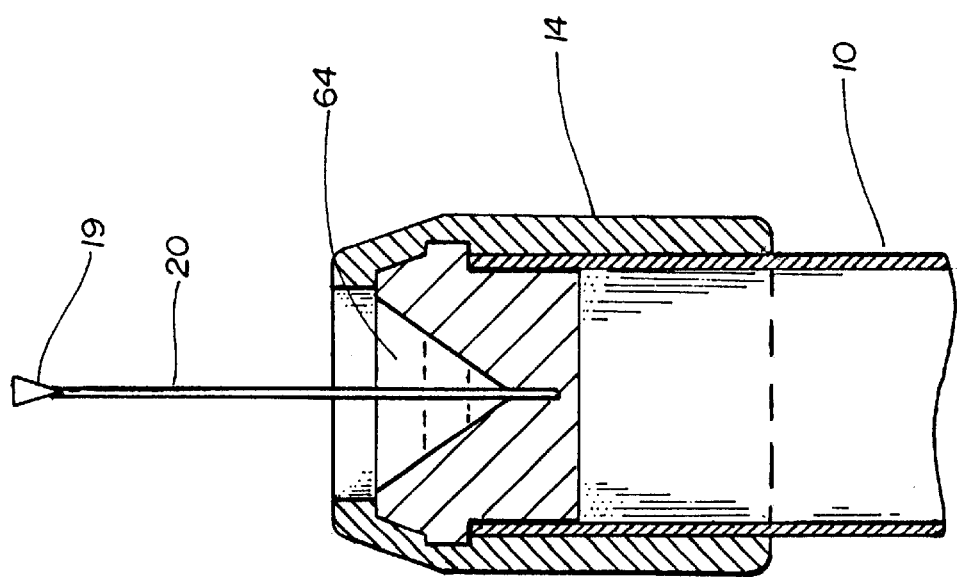
FIG. 12 is a diagrammatic illustration of a cannula partially projected through a plug's base section.

With the cannula 30 positioned in the socket's apex 65, the health care person is ready to initiate effecting the cannula's penetration of the plug's base section 60. To do this, the person further relatively displaces the container 10 and the syringe 12 with its cannula 30 axially toward each other thereby causing the distal end of the cannula to enter into the elastomeric material of the plug's base section 60. This causes the material of the plug 59 in the region closely adjacent the exterior surface of the cannula's tubular wall to be compressed and displaced radially outward therefrom but maintaining fluid and air tight engagement therewith. As the cannula progresses through the plug as shown in FIG. 12, the elastomeric material will continue to be displaced radially outward relative to the distal end of the cannula. The elastomeric material does not enter the cannula through its open end, regardless of whether it is of the squared-off configuration shown in FIG. 2 or of a rounded configuration such as that shown in FIG. 3. This results from the fact the elastomeric material has a cohesive characteristic which tends to maintain the material in a unitary body even though the cannula is effecting formation of a bore through the material to the extent of the small diameter of the cannula.

Figure 13:
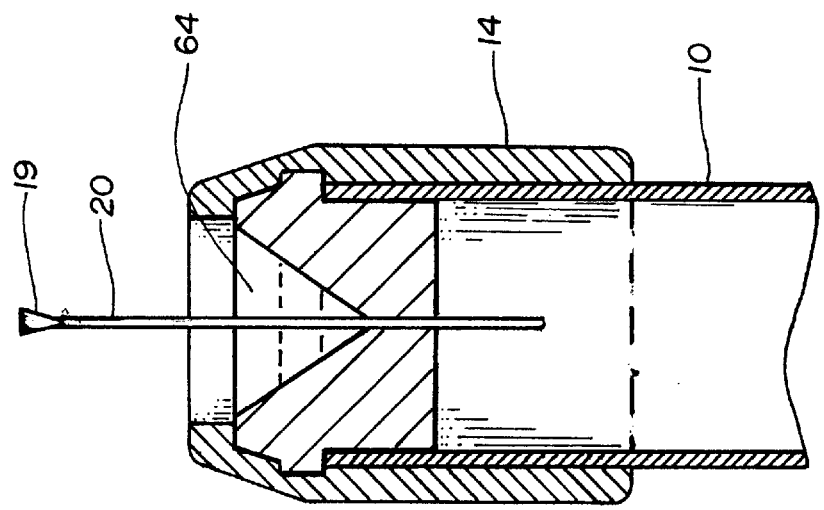
FIG. 13 is a diagrammatic illustration of a cannula having exited from a plug's base section with its distal end disposed interiorly of a collection container.

Ultimately, the cannula 30 exits from the plug's base section 60 at its end wall 66 into the interior of the container 10 as shown in FIG. 13. The person performing the fluids transfer operation can detect when exiting occurs both visually and by tactile sensing. Visual detection is possible as the container is formed from an optically transparent material. Tactile sensing results from the reduction in pressure required to effect axial displacement of the cannula. With the terminal end of the cannula now unobstructed, the fluid is automatically drawn into the container as a consequence of the vacumn existing in the evacuated container. In the case of laboratory tubes which are not evacuated but are otherwise functionally equivalent since they also contain the fluid, the fluid is expelled from the syringe by application of pressure to the syringe's piston rod 22 in an axially inward direction resulting in expelling of the fluid into the tube. The method of this invention also eliminates accidental sticks with these tubes.

With the fluid now transferred from the syringe 11 and into the collection container 10, the health care person is at the operating stage of removing the cannula from the closure member 14. This requires withdrawal of the cannula from the plug's base section 60 and is effected by axially displacing the syringe and the container 10 in relatively opposite directions whereby the cannula 30 is pulled out of the base section 60. As the cannula is withdrawn, its distal end is pulled from the bore which it had made in the base section during its entry step that was previously described. When the cannula's distal end is no longer disposed in that portion of the previously formed bore that it has just vacated, the elastomeric material that had been previously displaced radially outward is now enabled to expand radially inward thereby refilling the just vacated bore. As the opposing portions of the elastomeric material comes into contacting engagement, its cohesive characteristic results in reforming of an integral structure thereby effecting the resealing function.

It is the approaching stage of completing withdrawal of the cannula 30 from the base section 60 that will clearly demonstrate the greatly improved operational safety provided to the medical service person performing the fluids transfer operation through use of the described apparatus in performing transfer by employment of the method of this invention. The person performing the operation has no visual contact with the distal end of the cannula, or other means, to provide an indication of the position of the cannula relative to the wall surface 67 of the socket 64. Consequently, the person has no precise indication as to when the terminal end of the cannula will exit from the plug 59 and become unrestrained as to any lateral movement that may occur except for the restrictive effect of the axially extending wall of the socket and whatever directional control the person holding the syringe may be able to exercise when becoming abruptly aware of this situation. It is at this stage of operation when erratic movement of the cannula is most likely to be encountered as a result of the combined effects of concurrently releasing the cannula from both lateral and axial constraints along with the person's automatic reflexive reactions in counteracting undesired movement. This was described in the prior section relating to the background of the invention which discussed the accidental "stick" hazard that was associated with the prior art method employing a needle in performing a fluids transfer operation with respect to a fluids collection container.

Utilizing a blunt ended cannula, such as the typical configuration of either of the cannulas 30 or 35 shown in FIGS. 2 and 3, respectively, when employing the method of this invention effectively minimizes the likelihood of an accidental "stick" occurring. Although the cannula may initially move in an erratic manner upon exit from the plug's base section 60 for the reasons recited in the preceding and other paragraphs, this erratic movement is not likely to result in a "stick" even though the distal end of the cannula may contact a finger or other part of the hand of the health care person performing the transfer operation. The person performing the operation will naturally attempt exercising control over movement of the cannula to restrict its movement to a generally rectilinear path in axial alignment with the collection container and to control its speed of movement. But, the desired control over direction and speed cannot be assured during initial axial displacement away from the container after the distal end of the cannula exits from the base section 60 of the plug 59. Having a closure member 14 that includes a plug having a conical socket 64 extending even a short axial distance is advantageous as it does provide immediate restriction to lateral movement of the cannula upon its exit from the base section. This continues to be advantageous even though use of a blunt end cannula in accordance with the concept of this invention essentially eliminates the accidental "stick" hazard.

Avoidance of the accidental "stick" hazard is the primary objective of this invention and it is achieved with a substantial degree of success. Even though the cannula is likely to be displaced axially to an extent greater than the axial length of the socket of the closure member 14 and move radially outward to a position beyond the sleeve 58 where it could be displaced axially into contact with the person's hand or finger holding the container 10, depending upon the reflexive reactions of the health care person, the cannula is very unlikely to penetrate the protective glove of that person. The action which may occur is that the person pulling the cannula from the plug's base section 60 had been exerting a certain degree of force in an axially outward direction does not reduce their pulling force immediately upon the cannula's exit from the base section. Consequently, the speed of the cannula's axial movement is likely to at least momentarily accelerate resulting in the cannula being displaced to a position where its terminal end is not confined within the closure member's socket 64 formed in its plug 59. The health care person, upon sensing this undesired acceleration, will instinctively react by applying a counteracting force in the opposite axial direction. Should the cannula have concurrently become laterally displaced to a position that is radially outward of the closure member, a very possible situation, there is then nothing to obstruct axial displacement of the cannula into engagement with the finger or other part of the hand of the person holding the container 10.

That person holds the container by either partially encircling the container with the palm of the hand and utilizing the index finger and/or thumb in contacting engagement with the container's outer surface 55 or by holding it only with the thumb and fingers. Regardless of the particular holding technique utilized, the person will have a finger, thumb or portion of the hand's side edge surface positioned in close proximity to the sleeve of the closure member 14. If the cannula 30 becomes displaced radially outward of the closure member as described in the preceding paragraph, the terminal end of the cannula may be displaced a sufficient distance axially to contact the person's thumb, finger or side edge surface of the hand. Whether this occurs depends on the ability of the person to react with sufficient rapidity to regain control over movement of the cannula and syringe and prevent contacting engagement.

Regardless of whether contacting engagement occurs, use of this invention's apparatus in accordance with the inventive method effectively minimizes the likelihood of an accidental "stick". It is very improbable that sufficient force would be generated by a health care person while attempting to effect control over an erratically moving cannula as to result in a blunt end cannula penetrating the typical protective glove used in a fluids transfer and collection procedure of this nature and to then puncture that person's skin.

What is claimed is:

1. Apparatus for obtaining blood/body fluid from a patient and transfer thereof to a collection container comprising:

a fluids obtaining means, a fluids collection container, and a fluids transfer means for effecting transfer of fluid from said fluids obtaining means to said collection container, wherein said fluids obtaining means including a fluids securing device adapted to be placed in communication with a patient's body cavity containing the fluid to be obtained and a fluids displacing mechanism combined with a fluids retention component having a connecting device for coupling of said retention component to said fluids securing device, said fluids securing device being an elongated needle having mating means provided on its proximal end for removable mechanical interconnecting with the connecting device on said fluids retention component;

said fluids transfer means is adapted to be alternatively coupled to said connecting device in place of said fluids securing device, said transfer means comprising an elongated cannula having mating means attached to its proximal end and is adapted to be mechanically coupled with said connecting device in fluid tight engagement, said cannula having a blunt distal end; and said collection container being an elongated tube closed at one end with the opposite end being open whereby said cannula may be projected a distance interiorly of said container enabling fluid to flow from the retention component into the container while it is being held in an upright position by a health care person in their hand with its open end at the top.

2. Apparatus according to claim 1 having a closure member secured to said container at its open end and operable to form a fluid tight closure with said container, said closure member including a plug formed from an elastomeric material in an elongated cylindrical configuration adapted to be disposed in the open end of said container in frictionally engaged relationship, said elastomeric material having the characteristics of being axially penetratable by the distal end of said cannula and being self-resealable upon withdrawal of said cannula therefrom.

3. Apparatus according to claim 2 wherein said container is evacuated to form a vacumn therein adequate to draw fluid from said retention component through said cannula and into said container.

4. Apparatus according to claim 1 wherein said cannula's blunt distal end has an annular end face disposed in transversely extending relationship to the longitudinal axis of said cannula between longitudinally extending, spaced apart exterior and interior wall surfaces thereof.

5. Apparatus according to claim 4 wherein said cannula's annular end face is disposed in orthogonal relationship to said cannula's longitudinal axis.

6. Apparatus according to claim 1 wherein said cannula's blunt distal end has a transverse end face extending between exterior and interior axially extending wall surfaces thereof and is arcuately configured in an axially outward direction from the exterior to the interior wall surfaces.

7. The method of transferring a patient's blood/body fluid from fluid obtaining means used in obtaining a quantity of that fluid to a fluids collection container comprising the steps of:

drawing the fluid from the patient with a fluids securing device having a body penetrating element placed in communication with the patient's body cavity that has the fluid which is to be obtained and depositing it in a temporary fluid retention component;

removing the fluids securing device from operative fluids obtaining communication with the patient;

removing the body penetrating element from the temporary fluid retention component by means of a penetrating element gripping mechanism supported in association with a receptacle for receipt of the removed penetrating element thereby eliminating the need for manual contact with the penetrating element in effecting its removal and deposit in the receptacle;

coupling to the fluid retention component a cannula which has a distal end that is of a blunt configuration;

inserting the cannula's distal end into a fluids collection container having an open end thereof while the container is manually held in an upright position by a health care person with its open end at the top;

permitting the fluid to flow from the retention component and into the collection container; and withdrawing the cannula from the container after a predetermined quantity of fluid has been deposited therein and then discarding the cannula along with the retention component into a disposal receptacle.

8. The method according to claim 7 which includes forcibly causing the fluid to flow from the retention component into the collection container.

9. The method according to claim 7 which includes inserting the cannula into the collection container through a closure member secured to the container at its open end in fluid tight engagement therewith and effecting flow of fluid from the retention component into the collection container, said closure member having a plug through which the cannula is inserted positioned in the open end of the container in frictional engagement with its interior wall surface formed from an elastomeric material exhibiting the characteristics of being pentratable by the cannula with a blunt distal end and self-resealable upon withdrawal of the cannula.

10. The method according to claim 9 wherein the fluid is forcibly caused to flow from the retention component into the container.

11. The method according to claim 9 in which the collection container is initially in an evacuated state with a vacumn thus created in the container and which causes the fluid to flow from the retention component into the container after the distal end of the cannula is projected through the plug resulting in its terminal end becoming unobstructed to fluid flow.

* * * * *